United States Patent
Isogai et al.

(10) Patent No.: US 7,222,531 B2
(45) Date of Patent: May 29, 2007

(54) CAPACITIVE HUMIDITY SENSOR (75) Inventors: Toshiki Isogai, Nagoya (JP); Toshikazu Itakura, Toyota (JP)

(73) Assignees: Denso Corporation, Kariya (JP); Nippon Soken, Inc., Nishio (JP)

( * ) Notice: Subject to any disclaimer, the term of this patent is extended or adjusted under 35 U.S.C. 154(b) by 0 days.

(21) Appl. No.: 11/253,703

(22) Filed: Oct. 20, 2005

(65) Prior Publication Data
US 2006/0096370 A1    May 11, 2006

(30) Foreign Application Priority Data
Nov. 9, 2004    (JP)    ............... 2004-325518

(51) Int. Cl.
*G01N 22/27*    (2006.01)
(52) U.S. Cl. ................... 73/335.04; 73/335.02
(58) Field of Classification Search ............ 73/335.04, 73/335.02; 324/663, 664; 361/286
See application file for complete search history.

(56) References Cited

U.S. PATENT DOCUMENTS

| 6,580,600 | B2 | 6/2003 | Toyoda et al. |
| 2002/0114125 | A1 | 8/2002 | Toyoda et al. |
| 2004/0008041 | A1* | 1/2004 | Davis et al. ................. 324/664 |
| 2004/0008471 | A1* | 1/2004 | Davis et al. ............. 361/306.3 |
| 2004/0182153 | A1* | 9/2004 | Hamamoto ............... 73/335.04 |

* cited by examiner

*Primary Examiner*—Hezron Williams
*Assistant Examiner*—Ryan Christensen
(74) *Attorney, Agent, or Firm*—Posz Law Group, PLC

(57) ABSTRACT

A capacitive humidity sensor for detecting a humidity change includes a first sensor element having a first capacitance, a second sensor element having a second capacitance and connected in series with the first sensor element, and a humidity sensitive layer having a dielectric constant, which changes in accordance with humidity. The first and the second capacitances change with respect to the humidity change at a different rate. The humidity is detected using the different capacitances of the first and the second sensor elements. The humidity sensitive layer is formed to each sensor element so that each sensor element can be effectively protected.

20 Claims, 5 Drawing Sheets

CAPACITIVE HUMIDITY SENSOR

CROSS REFERENCE TO RELATED APPLICATION

This application is based on Japanese Patent Application No. 2004-325518 filed on Nov. 9, 2004, the disclosure of which is incorporated herein by reference.

FIELD OF THE INVENTION

The present invention relates to a capacitive humidity sensor, which detects a humidity change using a capacitance change.

BACKGROUND OF THE INVENTION

A capacitive humidity sensor, disclosed in U.S. Pat. No. 6,580,600 corresponding to JP-A-2002-243690, detects a change in relative humidity in the atmosphere using a capacitance change.

Figure 5A:
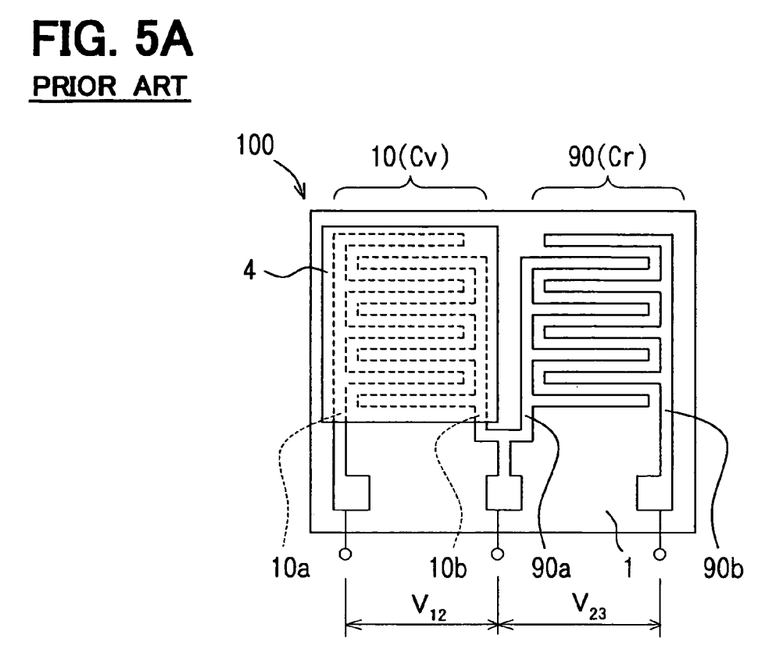
FIG. 5A is a plan view showing a capacitive humidity sensor according to prior art.

FIG. 5A is a plan view of a capacitive humidity sensor 100 similar to the sensor disclosed in U.S. Pat. No. 6,580,600. The sensor 100 includes a sensor element 10 and a reference element 90. The sensor element 10 has a pair of comb electrodes 10a, 10b, and the reference element 90 has a pair of comb electrodes 90a, 90b. The electrodes 10a, 10b and the electrodes 90a, 90b are disposed on the same surface of a semiconductor substrate 1.

Figure 5B:
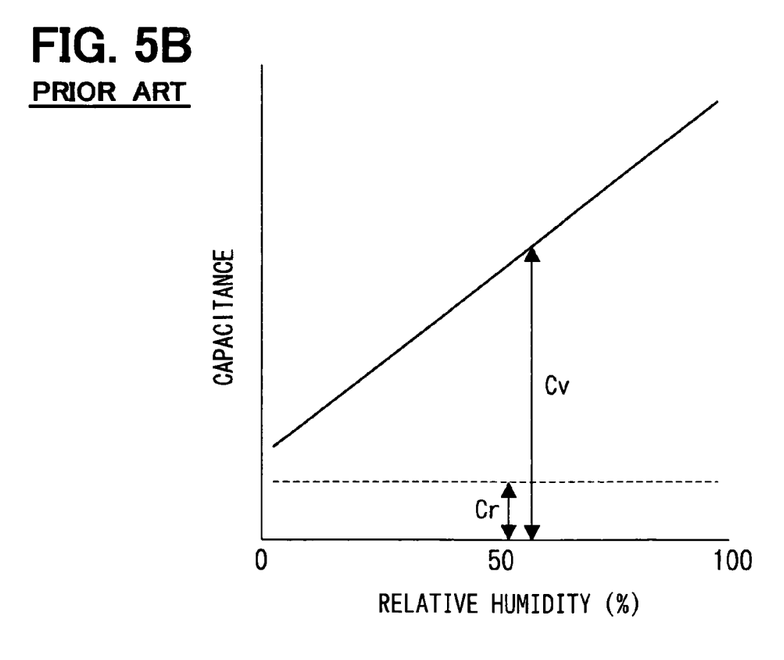
FIG. 5B is a graph showing a relationship between relative humidity and capacitances of a sensor element and a reference element of the sensor in FIG. 5A.

FIG. 5B shows a relationship between relative humidity and capacitances of the sensor element 10 and the reference element 90. A humidity sensitive layer 4 is formed on the electrodes 10a, 10b of the sensor element 10. In contrast, the humidity sensitive layer 4 is not formed on the electrodes 90a, 90b of the reference element 90. As shown in FIG. 5B, therefore, capacitance Cv of the sensor element 10 changes in accordance with a change in relative humidity, whereas capacitance Cr of the reference element 90 is constant relative to a change in relative humidity.

The sensor element 10 is connected in series with the reference element 90. In FIG. 5A, $V_{12}$ represents a voltage between the electrodes 10a, 10b of the sensor element 10. $V_{23}$ represents a voltage between the electrodes 90a, 90b of the reference element 90. A change of the Cv is reflected in a variation of the ratio of $V_{23}$ to $V_{12}$, because the Cv is represented by the following equation:

$$Cv = (V_{23}/V_{12})Cr$$

In the sensor 100, the capacitance Cv changed in accordance with a change in relative humidity is compared with the capacitance Cr, and then the variation of the ratio of $V_{23}$ to $V_{12}$ is detected. Relative humidity is calculated based on the variation of the ratio of $V_{23}$ to $V_{12}$ using a sensor signal processing circuit, which is formed on the substrate 1. Thus, the sensor 100 detects relative humidity in the atmosphere. The signal processing circuit is integrated with the substrate 1 so that the sensor 100 has a small size and can be manufactured at low cost.

As regards the sensor 100, however, it has been shown that the electrodes 90a, 90b of the reference element 90 were damaged and a value of the capacitance Cr of the reference element 90 was changed, after the sensor 100 was left for a long time under high-temperature and high-humidity condition. The electrodes 90a, 90b may be protected from damage by applying a protective material such as gel to surfaces of the electrodes 90a, 90b. In the case, however, the protective material may spread over the sensor element 10 adjacent to the reference element 90 because of the small size of the sensor 100. As a result, responsivity of the sensor element 10 is reduced. Further, manufacturing cost increases because of an additional process for applying the protective material to the electrodes 90a, 90b.

SUMMARY OF THE INVENTION

In view of the above-described problem, it is an object of the present invention to provide a capacitive humidity sensor, which can be used with stability for a long time under high-temperature and high-humidity condition.

According to an aspect of the present invention, a capacitive humidity sensor includes a first sensor element, a second sensor element, and a humidity sensitive layer having a dielectric constant, which changes in accordance with a change in relative humidity in the atmosphere. The first sensor element is connected in series with the second sensor element. The first sensor element has a capacitance that changes with respect to the relative humidity change at a first changing rate. Likewise, the second sensor element has a capacitance that changes with respect to the relative humidity change at a second changing rate. The first changing rate is different from the second changing rate, so that the capacitance of the first sensor element becomes different from the capacitance of the second sensor element at the same relative humidity. The capacitive humidity sensor detects the relative humidity in the atmosphere using the different capacitances.

The humidity sensitive layer can be disposed to cover both the first sensor element and the second sensor element. Therefore, the humidity sensitive layer protects electrodes of each sensor element so that the sensor can be used with stability for a long time under high-temperature and high-humidity condition. Further, reduction in responsivity and increase in manufacturing cost caused from an additional coating process can be avoided, because it is not required to apply a protective material to the sensor elements. Thus, the sensor can be manufactured in low cost.

The capacitance humidity sensor can be provided with a semiconductor substrate, and a protective layer disposed on the semiconductor substrate. In this case, the first sensor element can be a capacitive element having a pair of comb electrodes disposed on one surface of the semiconductor substrate to face each other with a predetermined gap, the second sensor element can be a capacitive element having comb electrodes disposed on the one surface of the semiconductor substrate to face each other with a predetermined gap, and the humidity sensitive layer can be disposed on the semiconductor substrate through the protective layer to cover the first sensor element and the second sensor element. Furthermore, a distance between adjacent comb-teeth portions of the comb electrodes of the first sensor element can be set different from a distance between adjacent comb-teeth portions of the comb electrodes of the second sensor element.

Furthermore, a length of comb-teeth portions of the comb electrodes of the first sensor element can be set different from a length of comb-teeth portions of the comb electrodes of the second sensor element, or/and a number of comb-teeth portions of the comb electrodes of the first sensor element can be set different from a number of comb-teeth portions of the comb electrodes of the second sensor element.

The humidity sensitive layer can be constructed of a single member formed on the first sensor element and the second sensor element. The comb electrodes of the first sensor element and the second sensor element are provided while an aluminum wiring for a semiconductor element, which is disposed on a different position of the substrate from the sensor elements, is performed. In this case, the protective layer can be made of silicon nitride and can be used as a protective layer of the aluminum wiring.

In the capacitance humidity sensor, the first sensor element can be made of a capacitive element having a bottom electrode and a top electrode, and the second sensor element can be made of a capacitive element having a bottom electrode and a top electrode. In this case, the protective layer and the humidity sensitive layer can be interposed between the bottom electrode and the top electrode of the first sensor element, and the protective layer and the humidity sensitive layer can be interposed between the bottom electrode and the top electrode of the second sensor element. Furthermore, a facing area of the bottom electrode and the top electrode of the first sensor element can be made different from a facing area of the bottom electrode and the top electrode of the second sensor element. In addition, the top electrodes of the first sensor element and the second sensor element can be integrally formed.

The bottom electrodes of the first sensor element and the second sensor element can be formed while an aluminum wiring for a semiconductor element, which is disposed on a different position of the substrate from the sensor elements, is performed. Furthermore, the protective layer can be made of silicon nitride and can be used as a protective layer of the aluminum wiring, and the humidity sensitive layer can be made of polyimide resin.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENTS (First Embodiment)

Figure 1A:
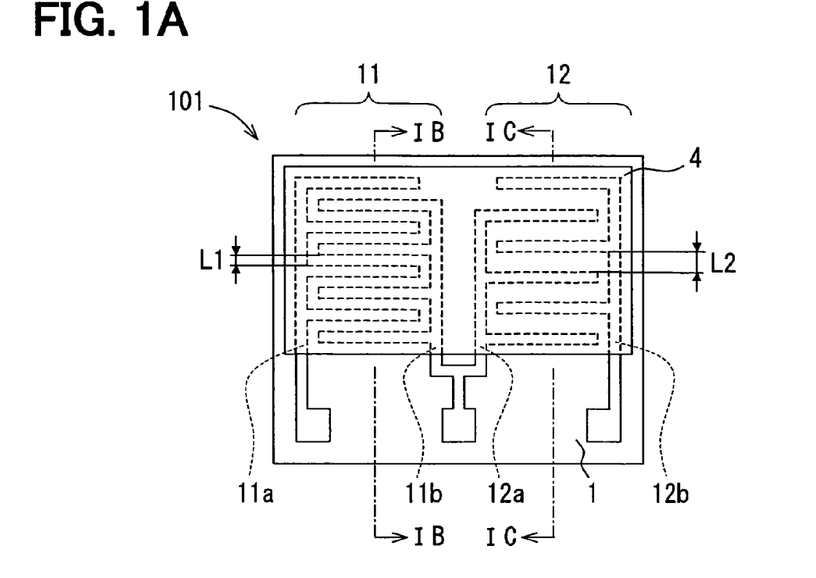
FIG. 1A is a schematic plan view showing a capacitive humidity sensor according to a first embodiment of the present invention.
Figure 1B:
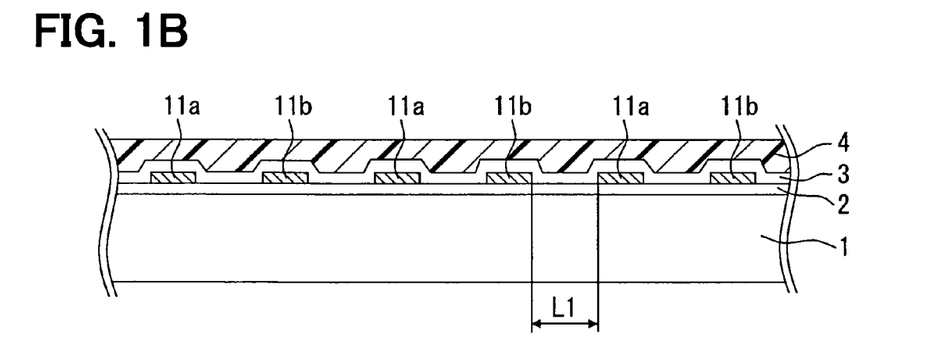
FIG. 1B is a cross-sectional view showing the sensor taken along line IB—IB in FIG. 1A.
Figure 1C:
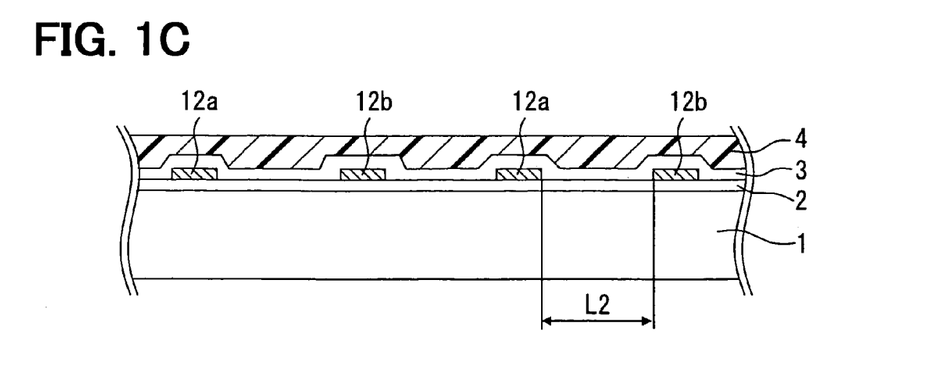
FIG. 1C is a cross-sectional view showing the sensor taken along line IC—IC in FIG. 1A.

FIGS. 1A to 1C show a capacitive humidity sensor 101 according to a first embodiment of the present invention. The sensor 101 includes a first sensor element 11 and a second sensor element 12. The first sensor element 11 and the second sensor element 12 have a pair of comb electrodes 11a, 11b and a pair of comb electrode 12a, 12b, respectively. The comb electrodes 11a, 11b and 12a, 12b are disposed on the same surface of a semiconductor substrate 1 through an insulating layer 2. The insulating layer 2 is made of oxide silicon ($SiO_2$). The comb electrodes 11a, 11b and 12a, 12b can be formed using the same process as, for example, aluminum wiring for a semiconductor element, which is formed on a different position of the substrate 1 from the sensor elements 11, 12. Thus, the comb electrodes 11a, 11b and 12a, 12b can be formed without an additional process, and thereby manufacturing process of the sensor 101 can be reduced.

In the sensor 101, a humidity sensitive layer 4 is formed on a semiconductor substrate 1 through an insulating layer 3 made of silicon nitride ($Si_3N_4$). The insulating layer 3 is a protective layer for the substrate 1 and protects the aluminum wiring. The humidity sensitive layer 4 has a dielectric constant, which changes in accordance with humidity. The humidity sensitive layer 4 can be made of polyimide resin, for example. As shown in FIG. 1A, the humidity sensitive layer 4 is formed integrally with both the first sensor element 11 and the second sensor element 12 to cover the comb electrodes 11a, 11b and 12a, 12b.

The first sensor element 11 has a capacitance Cv1 and a first changing rate at which the capacitance Cv1 changes with respect to a change in relative humidity. Likewise, the second sensor element 12 has a capacitance Cv2 and a second changing rate at which the capacitance Cv2 changes with respect to a change in relative humidity.

In FIG. 1A, L1 represents a separation distance between comb-teeth portion of the comb electrode 11a and comb-teeth portion of the comb electrode 11b. L2 represents a separation distance between comb-teeth portion of the comb electrode 12a and comb-teeth portion of the comb electrode 12b. In the sensor 101, the distance L1 is different from the distance L2, so that the first changing rate of the first sensor element 11 is different from the second changing rate of the second sensor element 12. Therefore, the capacitance Cv1 becomes different from the capacitance Cv2 at the same relative humidity.

Figure 2:
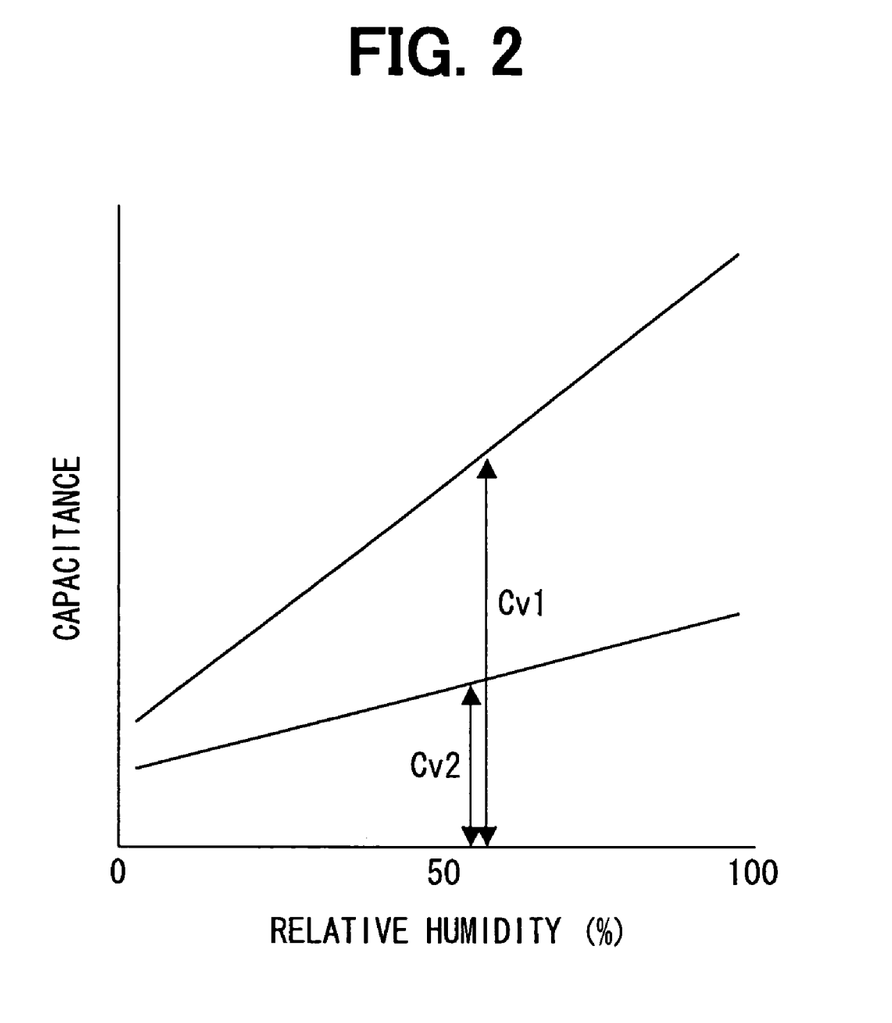
FIG. 2 is a graph showing a relationship between relative humidity and capacitances of a first sensor element and a second sensor element of the sensor shown in FIG. 1A.

FIG. 2 shows relationships between capacitance (Cv1) and relative humidity of the first sensor element 11, and between capacitance (Cv2) and relative humidity of the second sensor element 12. In the sensor 101, each sensor element 11, 12 is covered with the humidity sensitive layer 4 so that each capacitance Cv1, Cv2 changes in accordance with relative humidity in the atmosphere.

Further, the first changing rate of the first sensor element 11 is different from the second changing rate of the second sensor element 12. As shown in FIG. 2, therefore, the relationship between the capacitances Cv1, Cv2 and relative humidity is indicated as straight lines that have respectively different slopes and intercepts. In other words, the first sensor element 11 and the second sensor element 12 have respectively different sensibilities to a change in the relative humidity. Furthermore, the first sensor element 11 is connected in series with the second sensor element 12.

As described above, the capacitances Cv1, Cv2 can be detected as the ratio between a voltage of the first sensor element 11 and a voltage of the second sensor element 12. The relative humidity is calculated based on a variation of the ratio between the voltages, in a signal processing circuit formed on the substrate 1. Thus, the sensor 101 detects the relative humidity in the atmosphere.

In the sensor 101, each sensor element 11, 12 is covered with the humidity sensitive layer 4. The humidity sensitive layer 4 protects the electrodes 11a, 11b and 12a, 12b so that the sensor 101 can be used with stability for a long time under high-temperature and high-humidity condition. Reduction in responsivity and increase in manufacturing cost caused from an additional coating process can be avoided, because it is not required to additionally apply a protective material to the sensor elements 11, 12.

The humidity sensitive layer 4 is formed integrally with the first sensor element 11 and the second sensor element 12. Thus, the first sensor element 11 and the second sensor element 12 can be set equal in responsivity to a change in relative humidity and durability against the condition. In other words, if the distance L1 is set equal to the distance L2, the first changing rate becomes equal to the second changing rate because of the integration.

The dielectric constant of the humidity sensitive layer 4 changes in accordance with a change in relative humidity. The change of the dielectric constant is detected using variations in fringe capacitances between the comb electrodes 11a, 11b and between the comb electrodes 12a, 12b. In this case, it is required that the first sensor element 11 has a different sensitivity relative to a change in relative humidity, from the second sensor element 12. Therefore, it is required that the first sensor element 11 and the second sensor element have different capacitances from each other.

In the above-described sensor 101, as shown in FIG. 1A, the distance L1 between the comb-teeth portion of the electrode 11a and the comb-teeth portion of the electrode 11b is set different from the separation distance L2 between the comb-teeth portion of the electrode 12a and the comb-teeth portion of the electrode 12b. Thus, the first changing rate is different from the second changing rate, so that the capacitance Cv1 of the first sensor element 11 becomes different from the capacitance Cv2 of the second sensor element 12 at the same relative humidity.

The capacitance (sensitivity difference) of each sensor element 11, 12 can be adjusted to a desired value by adjusting a separation distance between the comb-teeth portions of the comb electrodes, a length and the number of the comb-teeth portion, a material and thickness of the humidity sensitive layer 4, or the like.

Figure 3A:
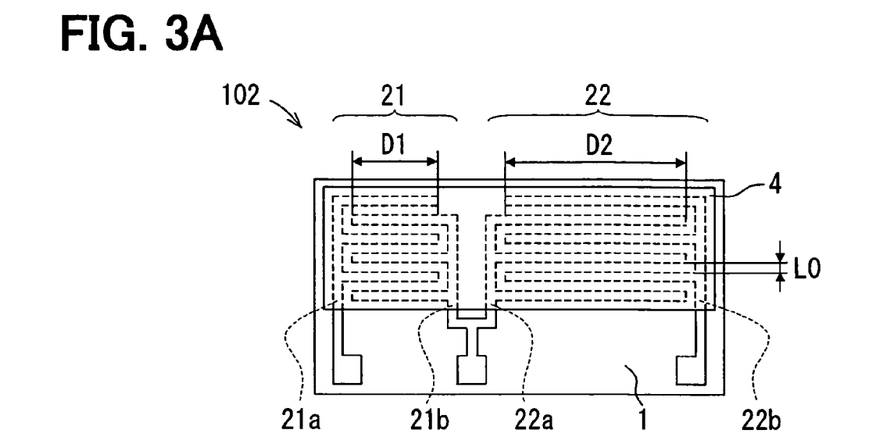
FIGS. 3A, 3B and 3C are plan views showing capacitive humidity sensors according to modifications of the first embodiment.

FIG. 3A shows a capacitive humidity sensor 102 that is a modification of the sensor 101. In the sensor 102, first and second sensor elements 21, 22 have the same separation distance L0 between comb teeth portions of a pair of comb electrodes 21a, 21b, and comb teeth portions of a pair of comb electrode 22a, 22b. However, a length D1 of the comb-teeth portions of the comb electrodes 21a, 21b is set different from a length D2 of the comb-teeth portions of the comb electrodes 22a, 22b. Thus, capacitances of the first sensor element 21 and the second sensor element 22 change with respect to a change in relative humidity at a different rate.

Figure 3B:
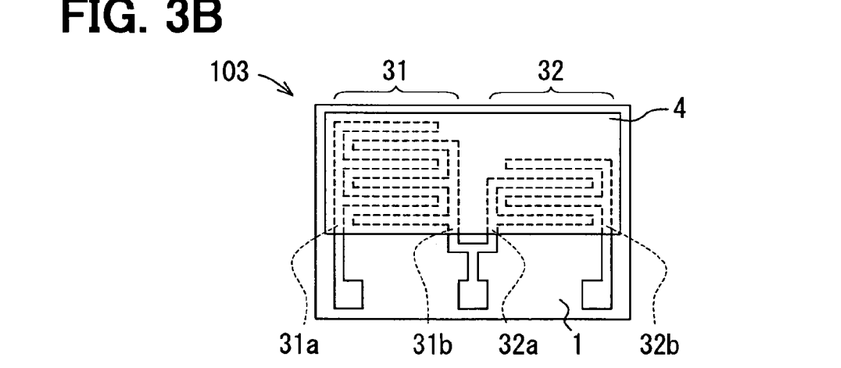

FIG. 3B shows a capacitive humidity sensor 103 that is another modification of the sensor 101. In the sensor 103, a separation distance between comb-teeth portions of a pair of comb electrodes 31a, 31b of a first sensor element 31 is set equal to a separation distance between comb-teeth portions of a pair of comb electrodes 32a, 32b of a second sensor element 32. Further, a length of the comb-teeth portions of the comb electrodes 31a, 31b of the first sensor element 31 is set equal to a length of the comb-teeth portions of the comb electrodes 32a, 32b of the second sensor element 32. As shown in FIG. 3B, however, the number of the comb-teeth portions of the comb electrodes 31a, 31b is set different from the number of the comb-teeth portions of the comb electrodes 32a, 32b. Thus, capacitances of the first sensor element 31 and the second element 32 change with respect to a change in relative humidity at a different rate.

Figure 3C:
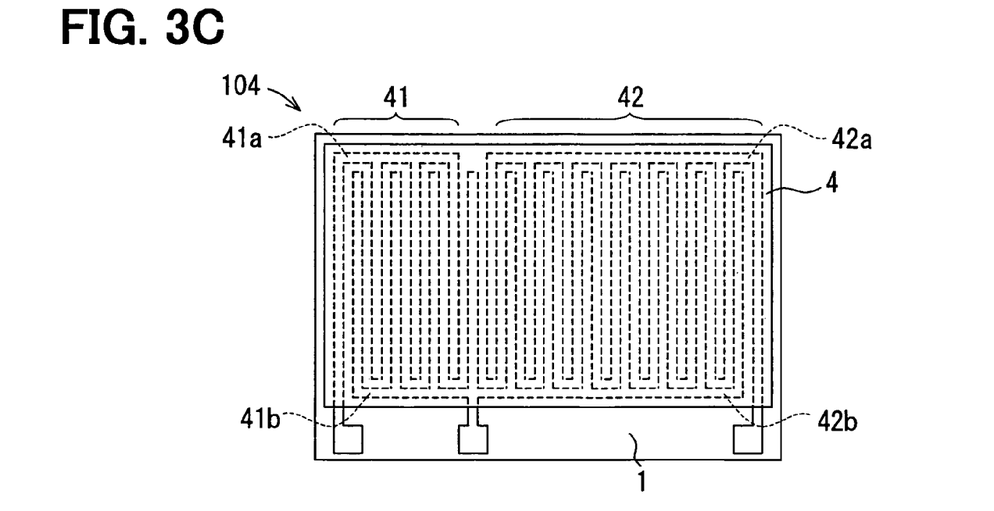

FIG. 3C shows a capacitive humidity sensor 104 that is another modification of the sensor 101. In the sensor 104, the number of comb-teeth portions of a pair of comb electrodes 41a, 41b of a first sensor element 41 is set different from the number of comb-teeth portions of a pair of comb electrodes 42a, 42b of a second sensor element 42. Thus, capacitances of the first sensor element 41 and the second element 42 change with respect to a change in relative humidity at a different rate. As shown in FIGS. 3B and 3C, however, the sensor 104 differs from the sensor 103 in the location of the electrode pads with respect to the direction in which the comb-teeth portions extend.

(Second Embodiment)

Figure 4A:
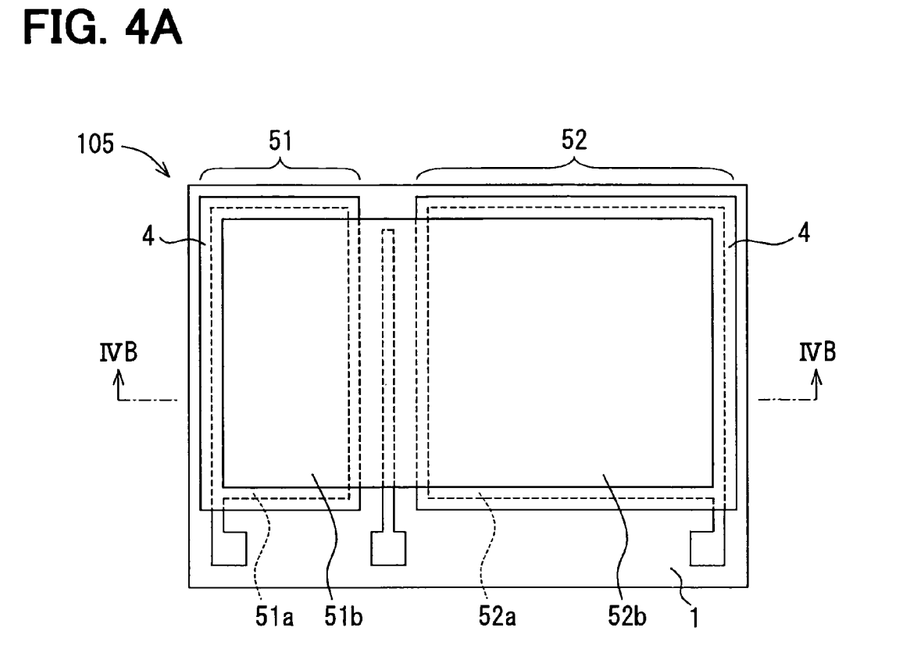
FIG. 4A is a plan view showing a capacitive humidity sensor according to a second embodiment of the present invention.
Figure 4B:
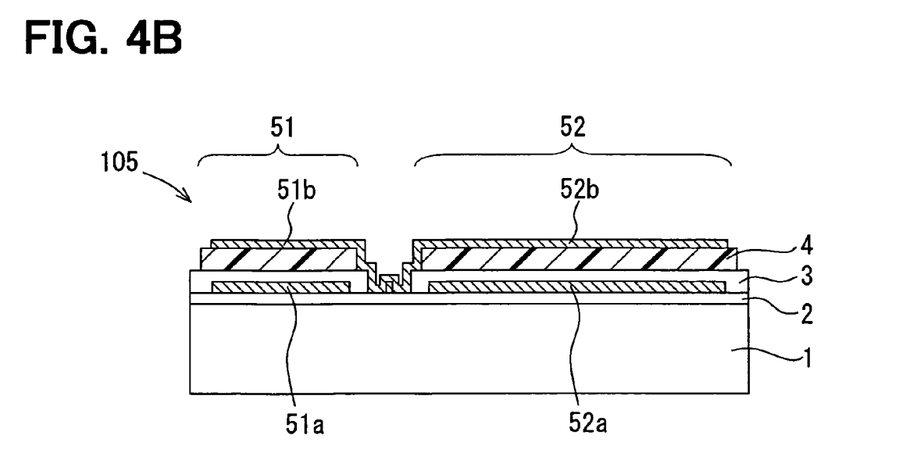
FIG. 4B is a cross-sectional view showing the sensor taken along line IVB—IVB in FIG. 4A.

FIGS. 4A and 4B show a capacitive humidity sensor 105 according to a second embodiment of the present invention.

The sensor 105 has a first sensor element 51 and a second sensor element 52, which are capacitive elements having stacked electrodes. The first sensor element 51 has a bottom electrode 51a and a top electrode 51b. The second sensor element 52 has a bottom electrode 52a and a top electrode 52b. A laminated member constructed of an insulating layer 3 and humidity sensitive layer 4 is interposed between the bottom electrodes 51a and the top electrodes 51b. Likewise, the laminated member is interposed between the bottom electrodes 52a and the top electrodes 52b. The insulating layer 3 can be made of silicon nitride ($Si_3N_4$), for example.

The bottom electrodes 51a, 52a are formed on a silicon semiconductor substrate 1 through an insulating layer 2, which is made of silicon oxide. The bottom electrodes 51a, 52a are formed in the same process as aluminum wiring for a semiconductor element, which is formed on a different position of the substrate 1 from the sensor elements 51, 52. Therefore, the bottom electrodes 51a, 52a can be formed while the aluminum wiring is formed. The insulating layer 3 is a protective layer for the substrate 1 and protects the aluminum wiring.

The humidity sensitive layers 4 can be made of polyimide resin, for example. As shown in FIG. 4B, in the sensor 105, the humidity sensitive layers 4 are separated from each other between the first sensor element 51 and the second sensor element 52. However, each sensitive humidity layer 4 can be formed at the same time and has the same thickness.

In the sensor 105, the facing area (overlapping portion) of the bottom electrode 51a and the top electrode 51b of the first sensor element 51 is set different from the facing area of the bottom electrode 52a and the top electrode 52b of the second sensor element 52. Thus, capacitances of the first sensor element 51 and the second element 52 change with respect to a change in relative humidity at a different rate.

Further, the first sensor element 51 is connected in series with the second sensor element 52. As described above, therefore, the capacitances of the sensor elements 51, 52 can be detected as the ratio between a voltage of the first sensor element 51 and a voltage of the second sensor element 52. The relative humidity is calculated based on the variation of the ratio of the voltages, in a signal processing circuit formed on the substrate 1. Thus, the sensor 105 detects the relative humidity in the atmosphere.

A high moisture resistant metal can be used as a material for the top electrodes 51b, 52b. The top electrodes 51b, 52b are integrally formed. Therefore, the first sensor element 51 and the second sensor element 52 can be set equal in responsivity to a change in relative humidity and durability against the condition. In other words, if the facing area (overlapping portion) of the first sensor element 51 is set equal to the facing area of the bottom electrode 52a, the capacitances of the first sensor element 51 and the second element 52 change with respect to a change in relative humidity at the same rate.

In the sensor 105, the humidity sensitive layers 4 are formed to each sensor element 51, 52. The humidity sensitive layers 4 protect the bottom electrodes 51a, 52a. In addition, the top electrodes 51b, 52b are made of high moisture resistant metal. Therefore, the sensor 105 can be used with stability for a long time under high-temperature and high-humidity condition. Because it is not required to apply a protective material to the sensor elements 51, 52, reduction in responsivity and increase in manufacturing cost caused from an additional coating process can be avoided. As a result, the sensor 105 has a small size and can be manufactured at low cost.

In the embodiments described above, the sensors are constructed with two sensor elements having different sensitivities to the relative humidity. In this case, difference in offset capacitance (capacitance when relative humidity is 0%) between the two sensor elements may be large. Therefore, enough output range may be not ensured in view of a detection circuit configuration.

Such changes and modifications are to be understood as being within the scope of the present invention as defined by the appended claims.

What is claimed is:

1. A capacitance humidity sensor for detecting a humidity change using a capacitance change, comprising:
   a semiconductor substrate;
   a protective layer disposed on the semiconductor substrate;
   a first sensor element, a capacitance of the first sensor element changing with respect to a humidity change at a first changing rate, the first sensor element including a capacitive element having a pair of comb electrodes disposed on one surface of the semiconductor substrate facing each other with a predetermined gap therebetween;
   a second sensor element being connected in series with the first sensor element, a capacitance of the second sensor element changing with respect to the humidity change at a second changing rate that is different from the first changing rate, the second sensor element including a capacitive element having comb electrodes disposed on the one surface of the semiconductor substrate facing each other with a predetermined gap therebetween; and
   a humidity sensitive layer having a dielectric constant which changes in accordance with the humidity change, the humidity sensitive layer being disposed on the semiconductor substrate through the protective layer to cover the first sensor element and the second sensor element, wherein
   a distance between adjacent comb-teeth portions of the comb electrodes of the first sensor element is different from a distance between adjacent comb-teeth portions of the comb electrodes of the second sensor element.

2. The sensor according to claim 1, wherein the humidity sensitive layer is a single member formed on the first sensor element and the second sensor element.

3. The sensor according to claim 1, wherein the comb electrodes of the first sensor element and the second sensor element are provided when an aluminum wiring for a semiconductor element, which is disposed on a different position of the substrate from the sensor elements, is formed, and the protective layer is made of silicon nitride and is used as a protective layer of the aluminum wiring.

4. The sensor according to claim 1, wherein
   the first sensor element has a bottom electrode and a top electrode,
   the protective layer and the humidity sensitive layer are interposed between the bottom electrode and the top electrode of the first sensor element,
   the second sensor element has a bottom electrode and a top electrode, and
   the protective layer and the humidity sensitive layer are interposed between the bottom electrode and the top electrode of the second sensor element.

5. The sensor according to claim 4, wherein
   a facing area of the bottom electrode and the top electrode of the first sensor element is different from a facing area of the bottom electrode and the top electrode of the second sensor element.

6. The sensor according to claim 4, wherein
   the top electrodes of the first sensor element and the second sensor element are integrally formed.

7. The sensor according to claim 4, wherein
   the bottom electrodes of the first sensor element and the second sensor element are provided when an aluminum wiring for a semiconductor element, which is disposed on a different position of the substrate from the sensor elements, is formed, and the protective layer is made of silicon nitride and is used as a protective layer of the aluminum wiring.

8. The sensor according to claim 1, wherein
   the humidity sensitive layer is made of polyimide resin.

9. A capacitance humidity sensor for detecting a humidity change using a capacitance change, comprising:
   a semiconductor substrate;
   a protective layer disposed on the semiconductor substrate;
   a first sensor element, a capacitance of the first sensor element changing with respect to a humidity change at a first changing rate, the first sensor element including a capacitive element having a pair of comb electrodes disposed on one surface of the semiconductor substrate facing each other with a predetermined gap therebetween;
   a second sensor element being connected in series with the first sensor element, a capacitance of the second sensor element changing with respect to the humidity change at a second changing rate that is different from the first changing rate, the second sensor element including a capacitive element having comb electrodes disposed on the one surface of the semiconductor substrate facing each other with a predetermined gap therebetween; and
   a humidity sensitive layer having a dielectric constant which changes in accordance with the humidity change, the humidity sensitive layer being disposed on the semiconductor substrate through the protective layer to cover the first sensor element and the second sensor element, wherein
   a length of comb-teeth portions of the comb electrodes of the first sensor element is different from a length of comb-teeth portions of the comb electrodes of the second sensor element.

10. The sensor according to claim 9, wherein
    the humidity sensitive layer is a single member formed on the first sensor element and the second sensor element.

11. The sensor according to claim 9, wherein
the comb electrodes of the first sensor element and the second sensor element are provided when an aluminum wiring for a semiconductor element, which is disposed on a different position of the substrate from the sensor elements, is formed, and
the protective layer is made of silicon nitride and is used as a protective layer of the aluminum wiring.

12. The sensor according to claim 9, wherein
the first sensor element has a bottom electrode and a top electrode,
the protective layer and the humidity sensitive layer are interposed between the bottom electrode and the top electrode of the first sensor element,
the second sensor element has a bottom electrode and a top electrode, and
the protective layer and the humidity sensitive layer are interposed between the bottom electrode and the top electrode of the second sensor element.

13. The sensor according to claim 12, wherein
a facing area of the bottom electrode and the top electrode of the first sensor element is different from a facing area of the bottom electrode and the top electrode of the second sensor element.

14. The sensor according to claim 12, wherein
the top electrodes of the first sensor element and the second sensor element are integrally formed.

15. The sensor according to claim 12, wherein
the bottom electrodes of the first sensor element and the second sensor element are provided when an aluminum wiring for a semiconductor element, which is disposed on a different position of the substrate from the sensor elements, is formed, and
the protective layer is made of silicon nitride and is used as a protective layer of the aluminum wiring.

16. The sensor according to claim 9, wherein
the humidity sensitive layer is made of polyimide resin.

17. A capacitance humidity sensor for detecting a humidity change using a capacitance change, comprising:
a semiconductor substrate;
a protective layer disposed on the semiconductor substrate;
a first sensor element, a capacitance of the first sensor element changing with respect to a humidity change at a first changing rate, the first sensor element including a capacitive element having a pair of comb electrodes disposed on one surface of the semiconductor substrate facing each other with a predetermined gap therebetween;
a second sensor element being connected in series with the first sensor element, a capacitance of the second sensor element changing with respect to the humidity change at a second changing rate that is different from the first changing rate, the second sensor element including a capacitive element having comb electrodes disposed on the one surface of the semiconductor substrate facing each other with a predetermined gap therebetween; and
a humidity sensitive layer having a dielectric constant which changes in accordance with the humidity change, the humidity sensitive layer being disposed on the semiconductor substrate through the protective layer to cover the first sensor element and the second sensor element, wherein
a number of comb-teeth portions of the comb electrodes of the first sensor element is different from a number of comb-teeth portions of the comb electrodes of the second sensor element.

18. The sensor according to claim 17, wherein
the humidity sensitive layer is a single member formed on the first sensor element and the second sensor element.

19. The sensor according to claim 17, wherein
the comb electrodes of the first sensor element and the second sensor element are provided when an aluminum wiring for a semiconductor element, which is disposed on a different position of the substrate from the sensor elements, is formed, and
the protective layer is made of silicon nitride and is used as a protective layer of the aluminum wiring.

20. The sensor according to claim 17, wherein
the first sensor element has a bottom electrode and a top electrode,
the protective layer and the humidity sensitive layer are interposed between the bottom electrode and the top electrode of the first sensor element,
the second sensor element has a bottom electrode and a top electrode, and
the protective layer and the humidity sensitive layer are interposed between the bottom electrode and the top electrode of the second sensor element.

* * * * *